United States Patent [19]

Kulczyk et al.

[11] Patent Number: 4,909,081
[45] Date of Patent: Mar. 20, 1990

[54] SYSTEMS FOR DETECTING MAGNETIC PARTICLES IN FLUIDS

[75] Inventors: Konrad Kulczyk, Bushey; Malcolm P. Perks, Dereham; George W. Smith, London, all of England

[73] Assignee: Schlumberger Industries Limited, Farnborough, England

[21] Appl. No.: 304,538

[22] Filed: Feb. 1, 1989

[30] Foreign Application Priority Data

Feb. 3, 1988 [GB] United Kingdom ............... 8802432

[51] Int. Cl.$^4$ ............................................. G01N 29/00
[52] U.S. Cl. ........................................ 73/597; 73/116
[58] Field of Search .................. 73/53, 64, 116, 119 R, 73/118.1, 120, 597, 602, 627, 629, 865.5, 865.8, 866; 340/627, 682

[56] References Cited

U.S. PATENT DOCUMENTS

| | | | |
|---|---|---|---|
| 3,878,103 | 4/1975 | Miller et al. | 340/627 |
| 4,112,735 | 9/1978 | McKnight | 73/865.5 |
| 4,176,545 | 12/1979 | Oddo | 73/64 |
| 4,620,185 | 10/1986 | Plahmer | 73/119 R |

FOREIGN PATENT DOCUMENTS

| | | | |
|---|---|---|---|
| 1808162 | 7/1969 | Fed. Rep. of Germany | 73/865.5 |
| 1354045 | 11/1987 | U.S.S.R. | 73/116 |

Primary Examiner—Robert R. Raevis
Attorney, Agent, or Firm—Sanford J. Asman

[57] ABSTRACT

An apparatus for detecting the presence of magnetic particles in a fluid is described. The apparatus uses a magnet which is mounted so that its field is transverse to the fluid flow, so that the magnetic field imparts a transverse velocity to any magnetic particles in the fluid. An ultrasound transducer mounted adjacent to the magnet. The ultrasound transducer is used to direct ultrasound energy into the moving fluid and to detect any particles having a velocity which is not in the direction of the main fluid flow, i.e., the velocity of a particle affected by the magnetic field will be detected by the ultrasound transducer as a result of the Doppler shift in the transmitted and reflected ultrasound frequency.

7 Claims, 3 Drawing Sheets

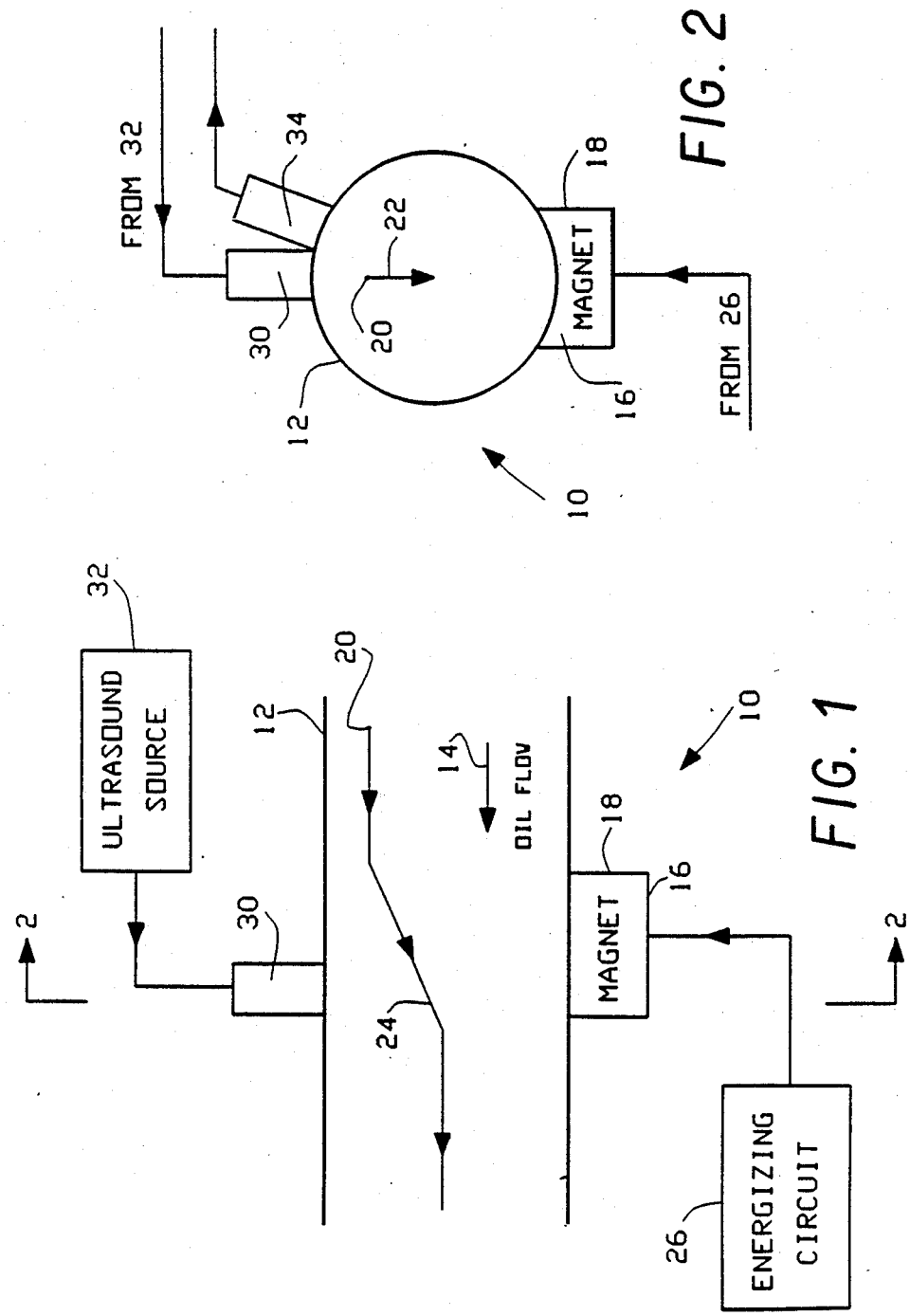

SYSTEMS FOR DETECTING MAGNETIC PARTICLES IN FLUIDS

BACKGROUND OF THE INVENTION

This invention relates to systems for detecting the presence of magnetic particles in fluids, and is more particularly but not exclusively concerned with such a system for use in an engine, typically a gas turbine engine, to detect the presence of magnetic particles in the oil used to lubricate the engine.

The relatively movable contact surfaces (eg in bearings, on shafts) of many engines are often made from magnetic materials, typically iron and/or nickel alloys. The quantity and size of magnetic particles in the oil used to lubricate such an engine are therefore frequently indicative of engine wear, since the particles typically originate by being worn or rubbed off the contact surfaces by friction. A sudden increase in the quantity and/or size of the particles can be an indication of rapidly increasing wear, or even incipient failure of a component of the engine, for example a bearing. It would therefore be highly desirable to be able to detect the presence of such magnetic particles "on line", ie while the engine is operating, so that if particles indicative of an incipient failure are detected, the engine could be shut down.

Various optical systems are known for detecting the presence of particles in fluid, eg by measuring the scattering of light by the particles. However, engine oil usually contains, in addition to magnetic particles, particles of carbon and other combustion products produced in the operation of the engine, and the known optical systems would not be capable of reliably distinguishing between the magnetic particles and those other particles.

It is therefore an object of the present invention to provide a system which can detect the presence of magnetic particles in a fluid, while ignoring the presence of non-magnetic particles.

SUMMARY OF THE INVENTION

According to the present invention, a system for detecting the presence of magnetic particles in a fluid comprises:

means for subjecting the fluid to a magnetic field so as to impart to any magnetic particles present therein a component of velocity in the direction of the magnetic field;

means for directing ultrasonic energy of known frequency into the fluid for scattering by such magnetic particles, the ultrasonic energy being directed such that the frequency of energy scattered by such magnetic particles is changed by said component of velocity by virtue of the Doppler effect; and means for receiving scattered ultrasonic energy and for detecting the presence of magnetic particles from changes in the frequency of the received energy.

In a preferred embodiment of the invention, the system further comprises means for defining a flow path for the fluid, the means for subjecting the fluid to a magnetic field comprising means for establishing a magnetic field transverse to said flow path.

The means for subjecting the fluid to a magnetic field may comprise a permanent magnet. Alternatively and preferably, it may comprise an electromagnet, and means for selectively energising and de-energising the electromagnet.

The receiving and detecting means may conveniently comprise at least one band pass filter, which selectively passes the expected Doppler-shifted frequency for a given size range of the magnetic particles, and may further include an integrator for integrating the output of the filter over a predetermined period of time. Additionally, the ultrasonic energy may be emitted in the form of pulses (each containing said known frequency), in which case the receiving and detecting means may further comprise means for counting the received scattered pulses.

BRIEF DESCRIPTION OF THE DRAWING

The invention will now be described, by way of example only, with reference to the accompanying drawings, of which:

FIG. 1 is a much simplified sectional view of a debris monitoring system in accordance with the present invention, for detecting magnetic particles in oil flowing in the lubrication system of a gas turbine engine;

FIG. 2 is a section on the line 2—2 of FIG. 1;

DETAILED DESCRIPTION OF AN EXEMPLARY EMBODIMENT

The debris monitoring system shown in FIGS. 1 and 2 is indicated generally at 10, and comprises a short section of pipe 12 adapted to be coupled in series in the lubrication system of a gas turbine engine, downstream of the bearings and other parts being lubricated. The oil flowing in the lubrication system therefore flows through the pipe 12, typically in the direction indicated by the arrow 14.

Figure 4:
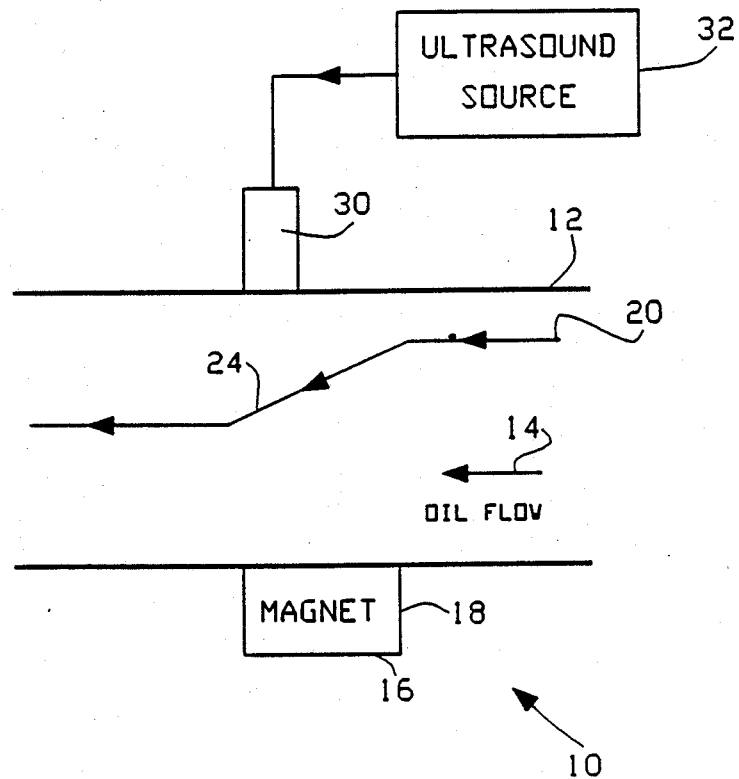
FIG. 4 is similar to FIG. 1, except that it illustrates the use of a permanent magnet.

One pole 16 of a powerful electromagnet 18 is disposed adjacent the pipe 12, so as to exert, when the electromagnet is energised, a powerful attractive force on any magnetic particles entrained in the oil. While the magnet 18 is preferably an electromagnet, alternatively, a permanent magnet, as shown in FIG. 4, could be used. In such event, of course, there would be no need to energize the magnet 18. As will be discussed hereinafter, there are advantages to using an electromagnet, as illustrated in FIG. 1, so the remainder of the discussion of the preferred embodiment will be limited to the use of an electromagnet.

Such a magnetic particle is indicated at 20 in FIGS. 1 and 2, and it can be seen that as it passes the pole 16 of the energised electromagnet 18, the attractive force exerted by the electromagnet accelerates the particle transversely (ie radially) of the pipe 12. The particle 20 thus acquires a transverse velocity component indicated by the arrow 22 in FIG. 2, and follows the path indicated at 24 in FIG. 1. In the preferred embodiment of the invention, the electromagnet 18 is arranged to produce a sufficiently strong attractive force to cause the particle 20 to acquire a transverse velocity of the order of 0.01 to 0.10 meters per second, which can require a flux density of up to about 1 tesla, depending on the size of the pipe 12 and the size of the particles to be detected. The electromagnet 18 is periodically energised by current supplied by a switchable energising circuit 26, periodic energisation being used (rather than continuous energisation) to reduce the tendency of the magnetic particles to accumulate on the pole 16.

A piezo-electric ultrasonic transducer 30 is acoustically coupled to the pipe 12 in substantially the same radial plane as the pole 16 of the electromagnet 18. The transducer 30 is energised by a signal source 32, which causes it to emit ultrasonic energy, either in pulses or continuously, substantially radially into the oil flowing in the pipe 12, at a frequency in the range 0.5 MHz to 5 MHz, typically around 1.0 MHz. Further, the transducer 30 is designed to known manner to focus the ultrasonic energy at a selected region in the pipe 12, where the transverse velocity components of particles such as the particle 10 are expected to be greatest.

The ultrasonic energy directed into the oil tends to be scattered by particles of appropriate size entrained in the oil. Typically, these particles will be in the size range 50 microns to 500 microns, and will either be magnetic like the particle 20, or of carbon or other non-magnetic material: however, only the magnetic particles will have a significant transverse component of velocity, since only they are affected by electromagnet 18.

A second piezo-electric transducer 34 is acoustically coupled to the pipe 12 in the same radial plane as the transducer 30. The transducer 34 is similar to the transducer 30, but acts as a receiver to receive ultrasonic energy scattered by the particles entrained in the oil. The transducer 34 is also focussed, again in known manner, to preferentially receive ultrasonic energy coming radially from the region on which the transducer 30 is focussed; and the angle between the transducers 30 and 34 (measured circumferentially of the pipe 12) is selected, by experiment if necessary, to enhance the reception of ultrasonic energy scattered by the particles.

Figure 3:
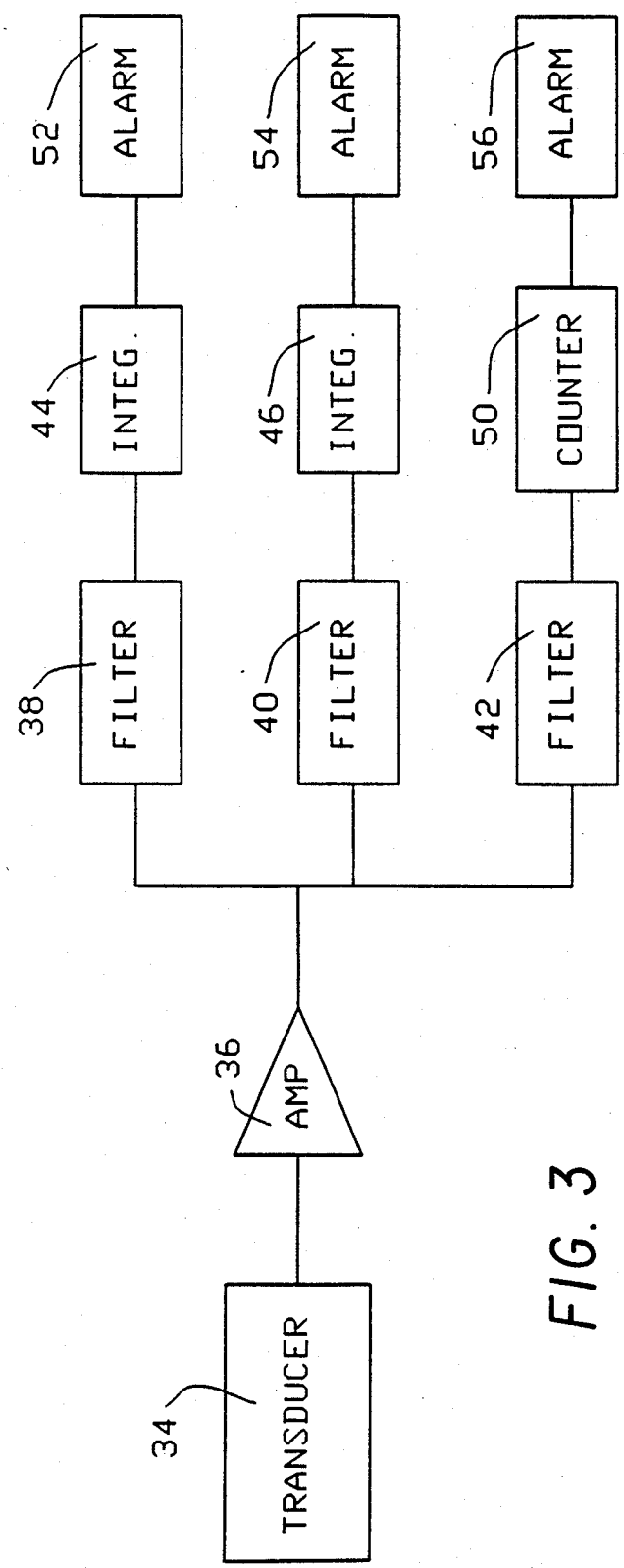
FIG. 3 is a simplified circuit diagram of a circuit forming part of the system of FIGS. 1 and 2.

Any ultrasonic energy scattered from particles having a transverse (or radial) velocity component, ie magnetic particles, will be subject to a Doppler shift (ie a frequency change) dependent upon the magnitude of the transverse velocity component, and it is this frequency change which enables the magnetic particles to be distinguished from non-magnetic ones. To detect this frequency change, the output of the transducer 34 is coupled via an amplifier 36 to a set of band-pass filters 38, 40, 42 (FIG. 3).

It wll be appreciated that the magnitude of the Doppler shift will be dependent upon the transverse velocity component of the particles, which in turn depends on the strength of the magnetic field produced by the electromagnet 18, the viscosity of the oil and the size of the particles. The first two of the factors affecting the transverse velocity component are substantially fixed design parameters, so in practice there is a range of Doppler shifts corresponding to the different sizes of the particles. The pass bands of the filters 38, 40, 42 are thus selected to correspond to different ranges of particle size. The filter 38 corresponds to the smallest detectable particles, and its output is connected to an integrator 44. The filter 40 corresponds to somewhat larger particles, and its output is connected to an integrator 46. Finally, the filter 42 corresponds to the largest particles, and its output is connected to a counter 50. The respective outputs of the integrators 44, 46 and the counter 50 are coupled to respective alarms 52, 54, 56.

In operation, and assuming that the transducer 30 is continuously energised, the integrators 44, 46 integrate the signals at the outputs of their respective filters, and thus accumulate respective signals representative of the total quantity of particles detected in their respective size ranges. The integrators are periodically reset, and as long as the quantity of particles detected in the intervals between resets is below a level representative of normal engine wear, the outputs of the integrators do not reach a level sufficient to trigger the alarms 52, 54. However, if the rate of particle detection increases above the normal engine wear level, one of the alarms 52, 54 will be triggered to warn of excessive engine wear.

When the transducer 30 is operated in the pulsed mode, it can effectively be used to count the largest particles. In that case, the count accumulated in the counter 50 is representative of the number of the largest particles detected. The counter 50 is also periodically reset, the reset interval being selected such that if excessive engine wear occurs, the counter will overflow before the end of the interval and operate the alarm 56.

Several modifications can be made to the described embodiment of the invention. In particular, in some configurations it is possible to omit the transducer 34 and to use the transducer 30 as both an emitter and receiver of the acoustic energy. Further, the frequencies at the output of the transducer 34 can clearly be heterodyned down, eg by mixing, for ease of subsequent processing.

We claim:

1. A system for detecting the presence of magnetic particles in a fluid comprising:
   means for subjecting the fluid to a magnetic field so as to impart to any magnetic particles present therein a component of velocity in the direction of the magnetic field;
   means for directing ultrasonic energy of known frequency into the fluid for scattering by such magnetic particles, the ultrasonic energy being directed such that the frequency of energy scattered by such magnetic particles is changed by said component of velocity by virtue of the Doppler effect; and
   means for receiving scattered ultrasonic energy and for detecting the presence of magnetic particles from changes in the frequency of the received energy.

2. A system as claimed in claim 1, further comprising means for defining a flow path for the fluid, the means for subjecting the fluid to a magnetic field comprising means for establishing a magnetic field transverse to said flow path.

3. A system as claimed in claim 1, wherein the means for subjecting the fluid to a magnetic field comprises a permanent magnet.

4. A system as claimed in claim 1, wherein the means for subjecting the fluid to a magnetic field comprises an electromagnet, and means for selectively energising and de-energising the electromagnet.

5. A system as claimed in claim 1, wherein the receiving and detecting means comprises at least one band pass filter, which selectively passes a frequency dependent upon the expected Doppler-shifted frequency for a given size range of the magnetic particles.

6. A system as claimed in claim 5, wherein the receiving and detecting means further includes an integrator for integrating the output of the filter over a predetermined period of time.

7. A system as claimed in claim 5, wherein the ultrasonic energy is emitted in the form of pulses, and the receiving and detecting means further comprises a counter connected to the output of the filter, for counting the received, scattered, pulses.

* * * * *